United States Patent [19]

Wilson et al.

[11] Patent Number: 5,087,451
[45] Date of Patent: Feb. 11, 1992

[54] TREATMENT OF PERIODONTAL DISEASE

[75] Inventors: Michael Wilson, London; Wilson Harvey, Dartford, both of England

[73] Assignee: National Research Development Corporation, London, England

[21] Appl. No.: 164,904

[22] Filed: Mar. 7, 1988

[30] Foreign Application Priority Data

Mar. 23, 1987 [GB] United Kingdom ............... 8706872

[51] Int. Cl.$^5$ .................. A01N 25/24; A61K 9/14; A61K 7/16
[52] U.S. Cl. .................. 424/407; 424/435; 424/484; 424/49; 514/184
[58] Field of Search ............ 514/184; 424/49, 54, 424/407, 435, 484

[56] References Cited

U.S. PATENT DOCUMENTS

| | | | |
|---|---|---|---|
| 4,105,758 | 8/1978 | Stanley | 424/49 |
| 4,223,033 | 9/1980 | Scheller | 424/7.1 |
| 4,348,378 | 9/1982 | Kosti | 424/7.1 |
| 4,444,746 | 4/1984 | Harvey et al. | 424/49 |
| 4,467,921 | 8/1984 | Greenland et al. | 206/524.4 |
| 4,533,484 | 8/1985 | Walles et al. | 252/117 |

FOREIGN PATENT DOCUMENTS

| | | | |
|---|---|---|---|
| 11663A | 6/1980 | European Pat. Off. | 514/184 |
| 2415093 | 10/1974 | Fed. Rep. of Germany | 514/184 |
| 985218 | 7/1951 | France | |
| 2203618 | 5/1974 | France | 514/184 |
| WO86/02831 | 5/1986 | PCT Int'l Appl. | 514/184 |
| 1319992 | 6/1973 | United Kingdom | 514/184 |

OTHER PUBLICATIONS

Kirk-Othmer's "Encyclopedia of Chemical Technology", Third edition, vol. 7, pp. 822–823, John Wiley & Sons (1979).

C. van Duijn, Jnr., "Diseases of Fishes", pp. 63, 87, 115, 145, 206, 300, 312 and 334–335, Iliffe Books, London (1973).

E. Djulgerova et al., Radiochem. Radional. Letters 58, 243–252 (1983), translation of relevant parts also supplied.

Lion Corp., Chemical Abstracts 100, 126742v (1984).

Lion Corp., Chemical Abstracts 102, 172447s (1985).

J. E. Jensen, Chemical Abstracts 88, 192f (1978).

A. Ogawa, Chemical Abstracts 95, 121174e (1981).

Löe et al., "Natural History of Periodontal Disease in Man", Journal of Clinical Periodontology, 13, pp. 431–440 (1986).

Johnson et al., "Detection of High-Risk Groups and Individuals . . . ", Ibid, 15, pp. 276–282 (1987).

McDowell, "Properties of Alginates", Alginate Industries Ltd., 4th ed., 1977, pp. 9–14.

Hanke & Katz, "An Electrolytic Method for Controlling . . . ", Arch. Biochem. Biophysics 1943, 2m 183–200.

*Primary Examiner*—Thurman K. Page
*Assistant Examiner*—Carlos Azpuru
*Attorney, Agent, or Firm*—Nixon & Vanderhye

[57] ABSTRACT

Periodontal disease is treated with a composition comprising a topically-retainable carrier such as an alginate gel and a non-toxic electron acceptor, such as a ferric compound or a redox organic dye, especially methylene blue or patent blue V, which does not supply molecular oxygen.

9 Claims, 3 Drawing Sheets

TREATMENT OF PERIODONTAL DISEASE

BACKGROUND OF THE INVENTION

1. Field of the Invention

This invention relates to the prophylactic or therapeutic treatment of periodontal disease, which is a gum disease.

2. Description of the Prior Art

The term "periodontal disease" as used herein includes any inflammatory disease of the periodontium (tooth-surrounding tissue). It is the most widespread human ailment affecting, to varying degrees of severity, the entire population. Chronic inflammatory periodontal disease (CIPD) is the major cause of tooth loss in adults. CIPD is the direct result of the accumulation of dental plaque between the "gum" and the tooth, i.e. in the gingival crevice. The microflora of this plaque is extremely complex, more than 250 component bacterial species having been described. It is not certain which of them cause the disease. There is, however, one point on which all investigators agree: the flora of the healthy gingival sulcus is sparse and consists largely of aerobic and facultative Gram-positive bacteria, while in the diseased state, when the sulcus becomes a crevice or pocket, there is a pronounced increase in the proportion of anaerobic and microaerophilic bacteria: Loesche et al, Journal of Periodontology 56, 447-456 (1985) and M. G. Newman, Journal of Periodontology 56, 734-739 (1985). The proportion of anaerobes increases with the severity of the disease. Those of the genus Bacteroides are considered to be among the important pathogens.

Attempts have been made to combat CIPD by preventing or reversing this increase in the proportion of anaerobic bacteria in the gingival crevice by removing the plaque, a tedious, labour-intensive and time-consuming process; by using antiseptics or antibiotics, an inadvisable course since it invariably leads to the development of a resistant microflora; or by applying to that locus a molecular oxygen-supplying substance, for example chromic acid; potassium permanganate; sodium peroxyborate; sodium perborate; calcium hypochlorite; zinc peroxide; urea peroxide; hydrogen peroxide; or molecular oxygen itself.

Of the oxygen-supplying substances only hydrogen peroxide remains in clinical use; and the efficacy of this use is a source of controversy in the dental profession. The failure of this group of compounds to treat the disease effectively might be due to the transience of oxygen provision in the periodontal pocket, allowing the rapid re-establishment of an anaerobic environment and the consequent growth of the pathogenic anaerobes. In addition, these highly-reactive compounds are likely to damage the tissues of the periodontium and possibly aggravate the inflammation.

Specific prior art relating to the invention is referred to in a separate section following the "Summary of the invention", without which its relationship would not be apparent.

If the current enormous cost of restorative treatments for dental caries is not to be paralleled by similarly expensive periodontal surgery, applied to large sections of the population, less costly and more effective means of prevention and control of periodontal disease need to be developed.

SUMMARY OF THE INVENTION

This invention seeks to solve the problem by altering the environment of the gingival sulcus or crevice or periodontal pocket to create conditions which are inimicable to the anaerobic and microaerophilic bacteria referred to. It has been found that such an environment is created by a redox compound in its oxidised (electron-accepting) form, when topically applied to the above-mentioned site.

Accordingly, this invention provides a composition for use in the treatment of periodontal disease by topical administration to the above-mentioned site, which comprises a topically-retainable carrier and an electron acceptor which is non-toxic and which, on said topical application, does not supply molecular oxygen. The electron acceptor may comprise a non-toxic compound of a multivalent metal, for example, a transition metal such as iron (as Fe(III)), or it may comprise a non-toxic redox dye. The metallic compound is preferably insolubilised as an alginate.

The most convenient mode of application contemplated at present is by syringe into the gingival sulcus or crevice or periodontal pocket. For this purpose a sterile syringeable preparation is required, a feature which is believed to distinguish the composition per se from other compositions containing electron acceptors and intended for other purposes. Accordingly, the invention further provides a sterile syringeable composition, both per se and when used to treat periodontal disease, the composition comprising a topically-retainable carrier of syringeable fluidity and an electron acceptor as defined above.

Further Description of Prior Art

The UK priority application has been searched by an EPO Standard Search (RS 78484GB) and by computer. The EPO Standard Search was carried out on a claim 1 broader than now present, in that it referred to treatment of anaerobic and microaerophilic bacterial infections generally (as well as to periodontal disease by way of specific example). The following references were revealed by these and other searches.

The antibacterial action of dyes is discussed in Kirk-Othmer's "Encyclopedia of Chemical Technology" 3rd edition, 7, 822-823. Methylene blue (CAS RN=61-73-4) is mentioned as inhibitory for several pathogens including *Mycobacterium tuberculosis*. Methylene blue is also an antiseptic used in domestic fish tanks and is mentioned in "Diseases of fishes" by C. van Duijn Jnr., 3rd edition 1973, Iliffe Books, London, for use against several different diseases including infection by worms and sporozoa, see pages 63, 87, 115, 145, 206, 300, 312 and 334-335. E. Djulgerova et al., Radiochem. Radioanal. letters 58, 243-252 (1983) found that methylene blue fed to rats in their diet reduced dental caries.

Several references mention the use of dyes and pigments in toothpastes, some of which are redox dyes. See U.S. Pat. Nos. 4,444,746 (patent blue V=CAS RN 129-17-9), 4,223,003 (patent blue V=Blau ZN 3) and 4,467,921 (Patent blue V and indigo carmine=CAS RN 860-22-0), British specification 1,319,992 (indigo carmine=F D & C Blue No. 2 and ferric oxides), and Chemical Abstract 100, 126742v (1984) (indigo=CAS RN 482-89-3). Chemical Abstract 102, 172447s, (1985) describes a toothpaste containing gel particles made from yellow iron oxide and sodium alginate and coated with an inorganic material such as titanium dioxide.

When the teeth are brushed, for 2-2½ minutes, the coating is abraded, liberating the colour of the iron oxide pigment.

Patent blue V is known as a disclosing agent, see French Specification 2,203,618 and German OS 2,415,093.

U.S. Pat. No. 4,105,758 relates to anthraquinone dyes for removing dental calculus (mineral deposits containing calcium phosphate). European Specification 11,663A relates to a synergistic anti-plaque composition containing (a) tetradecylamine and (b) any of various specified metallic compounds including iron. Another Chemical Abstract, 88 192f (1978) relates to the binding of certain dyes to chlorhexidine, which is an ingredient of a mouthwash. The article is apparently concerned with brown discolorations seen on the teeth of patients who use chlorhexidine mouthwashes.

Alginates are, of course, well known gelling agents. Thus in the Chemical Abstract 102, 172447s (1985), already mentioned, the polymeric gel particles in the toothpaste are made from sodium alginate. British Specification 1,319,992, already mentioned, refers to various other gelling agents for incorporation in toothpaste. PCT Application WO 86/02831 relates to the use of agents which are chelators for calcium for adding to a toothpaste to combat dental plaque and proposes the use of low viscosity, water-soluble alginates for this purpose. Such compounds are therein described as distinguished from higher molecular weight alginates used as viscosity-adjusting agents in foods and toothpastes.

Two of the references cited by the EPO relate to the dressing of wounds. These are French Specification 985,218, which relates to a dressing of a mixture of water-insoluble and water-soluble alginates, preferably calcium and sodium, which consistently swells in body fluids, and Chemical Abstract 95, 121174e (1981) relating to the addition of magnetic substances, such as iron powder and a therapeutic agent to bandages. It is alleged that iron powder and methyl salicylate have a synergistic anti-inflammatory activity.

None of the above-cited references suggests that an electron acceptor would be effective against the particular combination of bacteria responsible for periodontal disease. Nor do they constitute fortuitous or accidental prior disclosures: merely brushing the teeth or using a disclosing agent will not deliver an effective dose of the active ingredient into the crevice or pocket. Accordingly, the invention does not extend to such non-specific methods of administration.

BRIEF DESCRIPTION OF THE ACCOMPANYING DRAWINGS

FIGS. 1 and 2 are schematic vertical sections of a tooth, underlying alveolar bone and surrounding gum, showing in FIG. 1 the normal undiseased periodontium and in FIG. 2 a diseased periodontium, to each of which gel has been applied in accordance with the teaching of the present invention, and FIGS. 3 and 4 are bar charts in which the effects of ferric and calcium alginates on two bacterial species, one of them implicated in periodontal disease (FIG. 4) and the other not (FIG. 3) are compared.

DESCRIPTION OF THE PREFERRED EMBODIMENTS

The electron acceptor may comprise the oxidised form of a redox organic dye. The dye may comprise a quinone-imine dye; for example, a thiazin such as methylene blue, or an oxazin such as CI mordant violet 54. The dye may comprise a phenylmethane dye; for example, a triaminotriphenylmethane such as patent blue V; a non-toxic indigo dye; or a quinone dye; for example, an anthraquinone.

Of these dyes, methylene blue and patent blue V are preferred, because they have a positive reduction potential and are non-toxic (they are accepted food additives). The typical reduction potential of a diseased periodontal pocket is believed to be less than $-185$ mv, whereas that of the healthy gingival crevice is $+75$ mv. The reduction potential of methylene blue is $+11$ mv and that of patent blue V is $+750$ mv. Indigo carmine has a low redox potential ($-125$ mv) and is less preferred. It appears, therefore, that the application of an electron acceptor or redox compound of reduction potential well above that prevailing in the anaerobic environment of the diseased site inhibits the growth of the anaerobic pathogens responsible for the disease therein. Preferably the reduction potential is from $-50$ mv upwards (more positive) up to 1000 mv.

Preferably the electron acceptor is insoluble in saliva and comprises the oxidised form of a redox dye and, desirably, is topically-retainable by formulation as a gel, such as an alginate gel.

Figure 1:
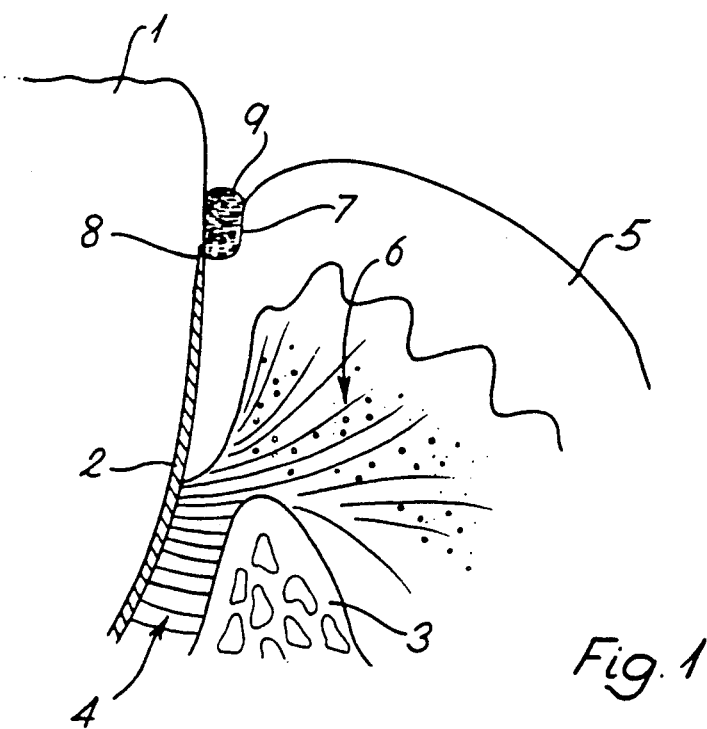
Figure 2:
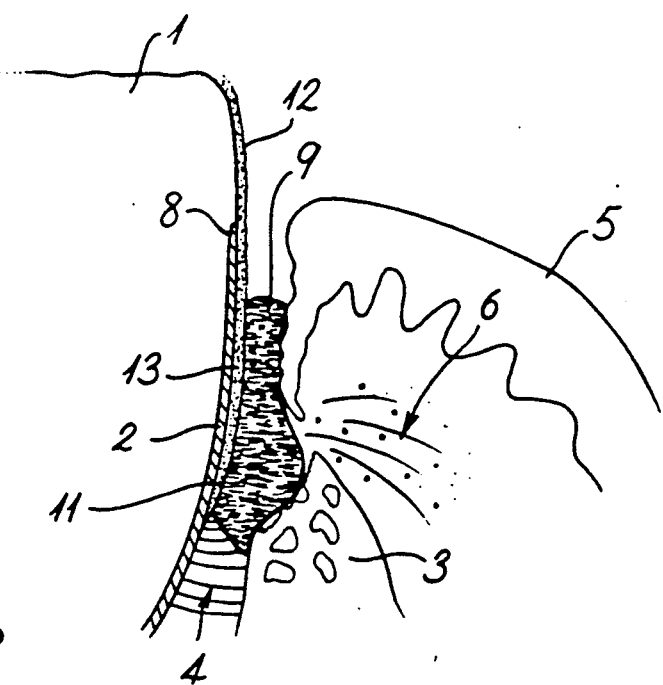

Referring to FIGS. 1 and 2 of the accompanying drawings, FIG. 1 shows the periodontium (tooth-surrounding tissues) of a normal, healthy person, illustrating the applicability of the invention in prophylaxis of periodontal disease. The tooth 1 having a cementum or thin outer layer of bone 2 (below the enamel) is held in place by the alveolar bone 3, against which it is cushioned by the periodontal ligaments 4. The gingiva (gum) comprises an oral epithelium 5 and vascular connective tissue 6 containing bundles of collagen fibres extending in approximately transverse directions to one another. The drawing shows the gingival sulcus 7, the small cavity between the epithelium and the tooth. The bottom of the sulcus, in the healthy mouth, abuts the tooth at the "gingival margin", 8. FIG. 1 shows gel of the invention 9 which has been introduced into the gingival sulcus.

FIG. 2 illustrates correspondingly a chronically diseased periodontium. The drawing is labelled correspondingly except that, with advance of the disease, the gingival sulcus in the healthy periodontium of FIG. 1 has expanded first into a crevice and then into the periodontal pocket 11 shown and that the tooth has become coated with a layer of dental plaque 12. That part which extends below the gingival margin 8 is described as sub-gingival plaque 13. The alveolar bone 3 has been eroded, thereby loosening the tooth. The connective tissue, which anchors the tooth, has also been partially eroded, with the result that the gum has a flabby appearance. (In healthy mouths, the collagen fibres maintain some rigidity in the gum).

Compositions of the invention may be applied topically, supra-gingivally to the gingival sulcus or sub-gingivally to the periodontal pocket or gingival crevice, for example from a syringe, to fill all the available space and thereby treat incipient or actual periodontal disease. The syringe can be filled with composition of the invention from a bottle or with cartridges of the composition.

The composition is preferably sterilised for storage, e.g. by autoclaving at 121° C. for 15 minutes.

An alternative formulation of the electron acceptor composition is as a dried strip (for example of dried impregnated alginate gel or ethylcellulose) or fibre (for example as an alginate wool) for insertion into the periodontal pocket. The electron acceptor may also be immobilised on a matrix such as an ion exchange resin. It can be incorporated in microcapsules, preferably of size between 10 and 500 microns; for a full description of microcapsules suitable for this purpose, see European Patent Specification 244118A (Pharmetrix Corporation). Another controlled release formulation for use in the invention is described in European Patent application 241178A (Rohto Pharmaceutical).

In vivo, gels of the present invention are retained in the periodontal pocket or gingival crevice, maximising tissue interaction and functioning as a long-acting reservoir. Furthermore, antibiotics and antiseptics need not be added, thereby lessening the effect on benign oral flora.

The dose of the active agent is any which is prophylactically or therapeutically effective as the case may be, normally between about 0.025 and 4 mg. per periodontium treated, preferably 0.25 to 2 mg. Conveniently from 25 to 200 microliters of gel containing from 0.1 to 2% by weight of the active agent, preferably about 1%, is used for each such unit dose.

The following Examples illustrate the invention.

EXAMPLES 1 and 2

Bacteria Tested

*Bacteroides intermedius*, an anaerobic organism considered to be of importance as a periodontal pathogen, was selected as a suitable test organism. *Escherichia coli*, a facultative organism which can metabolise aerobically or anaerobically, was used as control.

Culture Medium

Brain Heart Infusion sloppy agar (BHA), supplemented with 5% horse blood, was used as the culture medium. The medium, containing a variety of natural reductants and being sufficiently viscous to hinder the dissolution of atmospheric oxygen thereinto, is widely used to maintain cultures of anaerobic bacteria under ambient conditions.

Electron Acceptors

Ferric alginate was prepared by adding 0.2M ferric chloride to an equal volume of a 2% aqueous solution of sodium alginate. The resulting gel was filtered and washed with distilled water. A calcium alginate gel, as control, was prepared analogously.

Methylene blue was also used as an electron acceptor, a 4% solution being made up with distilled water. The control in this case was distilled water alone.

GROWTH EXPERIMENTS

1. Using Ferric Alginate as the Active Agent (a) 1 g, 2 g and 5 g of either ferric or calcium alginate (as control) were added to separate 15 ml. aliquots of BHA and inoculated with 200 $\mu$l of a 48 h culture of *B. intermedius*. An identical series of cultures was prepared and inoculated with 200 $\mu$l of an overnight culture of *E. coli*. Total viable counts were performed on the *B. intermedius* cultures after 3 and 5 days incubation at 37° C. In the case of *E. coli* (which is a much faster-growing organism) viable counts were performed only after overnight incubation. The concentration of ferric ions in the gel was determined colorimetrically using thiocyanate and was found to be 2.5 mg of ferric ions per g of gel.

(b) 5 g of each alginate was added to 5 ml of BHA and inoculated with 5 ml of the bacterial cultures. Viable counts were then performed on each of these as described above.

2. Using Methylene Blue as the Active Agent

4% methylene blue was added to separate 18 ml aliquots of BHA to give final concentrations of 0.2, 0.04 and 0.004%. These were inoculated with either *B. intermedius* or *E. coli* as described in 1a above. Viable counts were performed at various time intervals.

The results of Example 1 are presented graphically. From FIG. 3 it can be seen that the calcium alginate gel had no effect on the growth of *E. coli*. Similarly, 1 g and 2 g of ferric alginate gel had no effect; only in the culture containing 5 g of ferric alginate gel was any decrease in growth detected and this amounted to a reduction of 73% compared with the control culture. It can also be seen (FIG. 4) that calcium alginate gel had no effect on the growth of *B. intermedius* whereas 1 g and 2 g of ferric alginate gel had a marked effect reducing the viable count by 99% and 98% respectively. 5 g of ferric alginate reduced the viable count to less than 250 cfu/ml.

SURVIVAL EXPERIMENT

Figure 3:
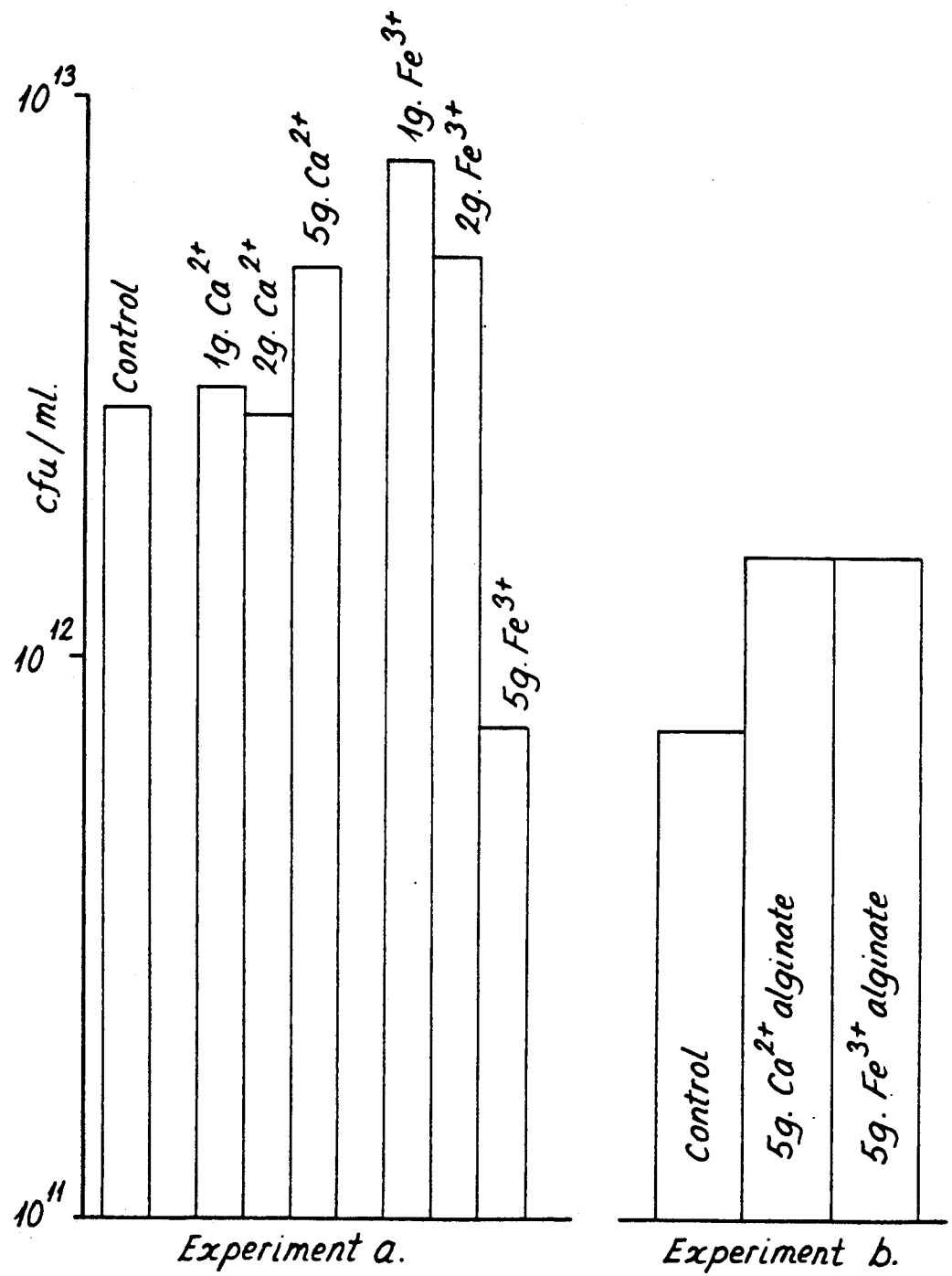
Figure 4:
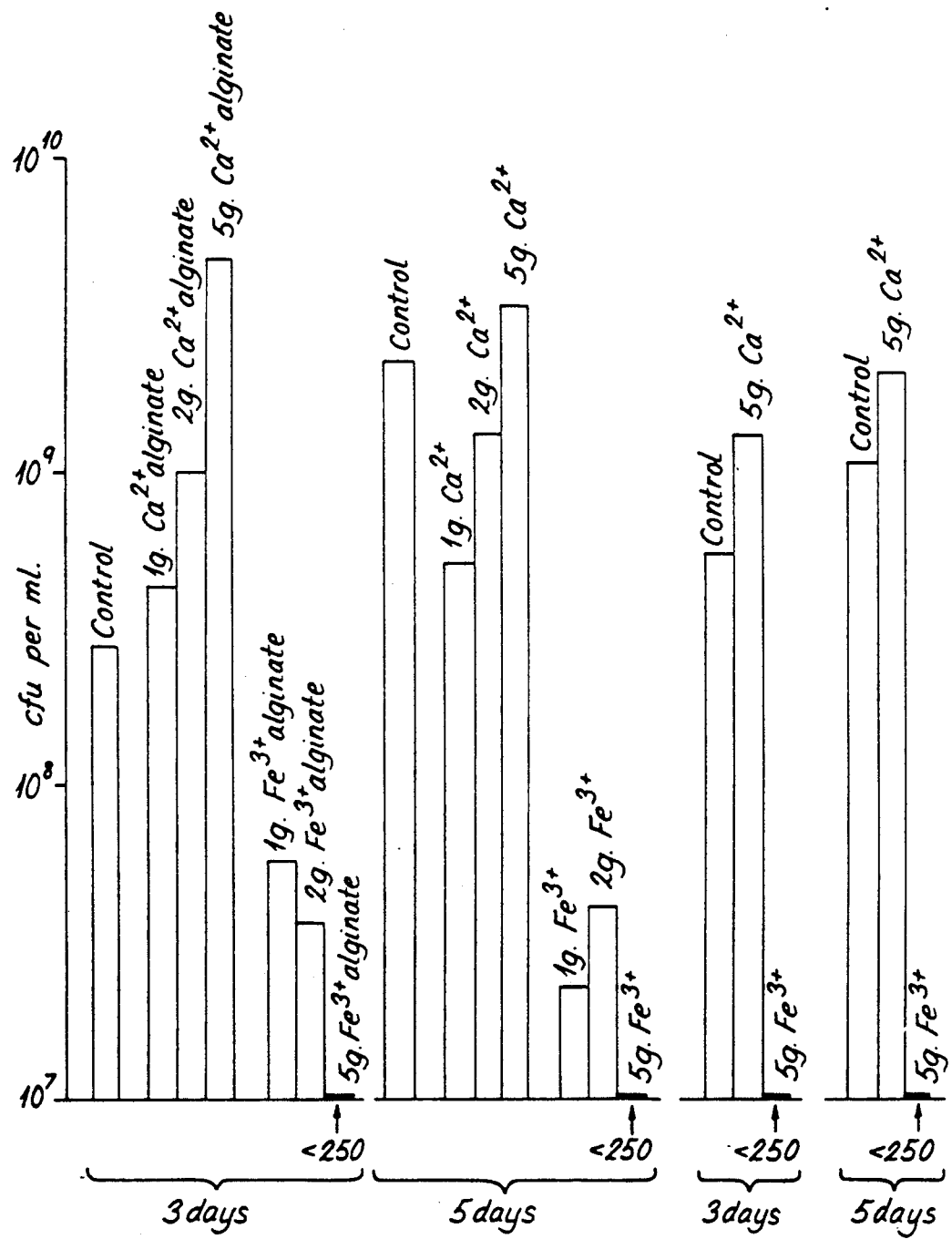

Experiment (b) was performed to determine the effect of the alginate gels on the survival of the two organisms. The alginate gels were added to comparatively large quantities of dense cultures of the bacteria. In FIG. 3 it can be seen that neither alginate gel had an effect on the *E. coli* cultures, whereas in the case of the *B. intermedius* the calcium alginate gel had no effect (FIG. 4) while the ferric alginate reduced the viable count to less than 250 cfu/ml).

The results of Example 2 are shown in Table 1 below.

From Table 1 it can be seen that methylene blue had no effect on the growth of *E. coli* at any of the concentrations tested. By contrast, methylene blue had a dramatic effect on the growth of *B. intermedius*. At the lowest concentration tested (0.004%), the viable count was reduced by 69% and 99.17% after 2 and 4 days incubation in one experiment and by 92.6% and 99.99% after 3 and 7 days incubation in the second experiment.

It will be seen that non-toxic Lewis acids can selectively inhibit the growth of anaerobic bacteria as found in periodontal disease, facultative bacteria being unaffected.

TABLE 1

| Organism | Viable count (cfu/ml) | % reduction |
|---|---|---|
| *E. coli* | | |
| control | 2.25 × 10$^{10}$ | |
| 0.2% | " | 0 |
| 0.4% | " | 0 |
| 0.004% | 3.25 × 10$^{10}$ | 0 |
| *B. intermedius* | | |
| control (2 day) | 2 × 10$^8$ | |
| 0.2% (2 day) | <250 | 100 |
| 0.04% (2 day) | 2.75 × 10$^4$ | 99.98 |
| 0.004% (2 day) | 6.25 × 10$^7$ | 69 |
| control (4 day) | 5.13 × 10$^8$ | |
| 0.2% (4 day) | <250 | 100 |
| 0.04% (4 day) | 2.5 × 10$^3$ | 99.99 |
| 0.004% (4 day) | 4.25 × 10$^6$ | 99.17 |
| *B. intermedius* | | |
| control (3 day) | 2.38 × 10$^8$ | |
| 0.2% (3 day) | <250 | 100 |
| 0.04% (3 day) | <250 | 100 |
| 0.004% (3 day) | 1.75 × 10$^7$ | 92.6 |

TABLE 1-continued

| Organism | Viable count (cfu/ml) | % reduction |
|---|---|---|
| control (7 day) | $2 \times 10^5$ | |
| 0.2% (7 day) | <250 | 100 |
| 0.04% (7 day) | <250 | 100 |
| 0.004% (7 day) | $7.5 \times 10^3$ | 99.99 |

EXAMPLES 3 to 5

In a clinical trial, 10 patients were treated, most of them having 4 test and 4 control diseased sites. 7 patients received methylene blue/alginate, 2 patients received patent blue V/alginate, and 1 patient received indigo carmine/alginate in their test sites. The control sites in all cases received sterile distilled water. The patients were seen at time 0 (initial appointment), 3 days, 7 days and 14 days. Medication (both control and test) continued up to day 7.

The significant investigations performed were bacteriological, these being the most reliable indicators of clinical efficacy in a short term trial such as this one.

The total proportions of anaerobes, Gram-negative anaerobes, facultatives, motiles, spirochaetes and cocci were measured. An improvement in periodontal health is reflected by a relative increase in the proportions of cocci or facultatives, or a decrease in the proportion of total anaerobes, Gram-negative anaerobes, motiles or spirochaetes.

A sensitive index of inflammation in periodontal disease is the rate of crevicular fluid flow. This fluid is an exudate from the normal sulcus and from the periodontal pocket; in the latter case it is greatly increased.

The results, Tables 2 to 4, below, are expressed as the % change compared with the pre-treatment (time 0) values. They show that the administration of methylene blue to periodontal pockets produces a highly significant beneficial effect. In all parameters measured the changes reached statistical significance, at some point in the trial. Similar good results were obtained in the case of patent blue V. In contrast, using indigo carmine, no significant improvements were found in the bacteriological or clinical parameters, indicating that a dye with so negative a reduction potential does not beneficially influence periodontal disease.

TABLE 2

Methylene blue
7 patients, 25 test sites, 25 control sites.

| | | mean % change from day 0 | | |
|---|---|---|---|---|
| | | day 3 | day 7 | day 14 |
| Total | control | −5 | −11 | −10 |
| anaerobes | test | −20 p = 0.23 (NS) | −39 p = 0.002 | −25 p = 0.064 (NS) |
| Gram-neg. | control | +13 | −2 | +4 |
| anaerobes | test | −8 p = 0.031 | −16 p = 0.068 (NS) | −11 p = 0.13 (NS) |
| Facultat. | control | +6 | +16 | 0 |
| | test | +19 p = 0.23 (NS) | +38 p = 0.019 | +26 p = 0.036 |
| Motiles | control | −4 | −11 | −16 |
| | test | −36 p = 0.001 | −44 p = 0.001 | −45 p = 0.001 |
| Spiros | control | −3 | −7 | −10 |
| | test | −22 p = 0.0045 | −31 p = 0.001 | −31 p = 0.019 |
| Cocci | control | −3 | +9 | +4 |
| | test | +27 p = 0.009 | +42 p = 0.006 | +31 p = 0.064 (NS) |
| CFF | control | +23.5 | +7.3 | −6.9 |
| | test | −36.1 p < 0.001 | −48.8 p < 0.01 | −59.1 p < 0.001 |

NS = not statistically significant at the 5% level.
CFF = crevicular fluid flow.

TABLE 3

Patent blue V
2 patients, 8 test sites, 8 control sites

| | | mean % change from day 0 | | |
|---|---|---|---|---|
| | | day 3 | day 7 | day 14 |
| Total | control | +13 | +9 | −9 |
| anaerobes | test | −11 p = 0.014 | −6 p = 0.016 | −40 p = 0.003 |
| Gram-neg. | control | +19 | −4 | +2 |
| anaerobes | test | −3 p = 0.012 | −31 p = 0.001 | −18 p = 0.014 |
| Facultat. | control | −7 | −16 | +9 |
| | test | +11 p = 0.306 (NS) | +10 p = 0.052 | +29 p = 0.019 |
| Motiles | control | −19 | 0 | −8 |
| | test | −44 p = 0.17 (NS) | −22 p = 0.014 | −23 p = 0.032 |
| Spiros | control | −19 | −6 | −8 |
| | test | −34 p = 0.17 (NS) | −18 p = 0.041 | −16 p = 0.065 (NS) |
| Cocci | control | +6 | +2 | −11 |
| | test | +41 p = 0.014 | +13 p = 0.025 | +9 p = 0.008 |
| CFF | control | −0.27 | −1.99 | −3.15 |
| | test | −2.62 p < 0.01 | −4.49 p < 0.02 | −5.14 p < 0.05 |

NS = not statistically significant at the 5% level.

TABLE 4

| | | Indigo carmine | | |
|---|---|---|---|---|
| | | 1 patients, 4 test sites, 4 control sites | | |
| | | mean % change from day 0 | | |
| | | day 3 | day 7 | day 14 |
| Total anaerobes | control | +59 | +15 | +24 |
| | test | +23 $p = 0.057$ (NS) | −23 $p = 0.171$ (NS) | −2 $p = 0.243$ (NS) |
| Gram-neg. anaerobes | control | +6 | −4 | +11 |
| | test | +17 $p = 0.343$ (NS) | −27 $p = 0.443$ (NS) | −22 $p = 0.2$ (NS) |
| Facultat. | control | −59 | −15 | −17 |
| | test | −23 $p = 0.057$ (NS) | +23 $p = 0.171$ (NS) | +2 $p = 0.443$ (NS) |
| Motiles | control | −2 | −18 | −19 |
| | test | −11 $p = 0.5$ (NS) | +14 $p = 0.43$ (NS) | −14 $p = 0.24$ (NS) |
| Spiros | control | −3 | −6 | −7 |
| | test | −4 $p = 0.43$ (NS) | −3 $p = 0.43$ (NS) | −4 $p = 0.5$ (NS) |
| Cocci | control | +20 | +21 | +11 |
| | test | +35 $p = 0.44$ (NS) | +4 $p = 0.2$ (NS) | +14 $p = 0.44$ (NS) |
| CFF | control | +9 | −49 | −49 |
| | test | −21 $p > 0.1$ (NS) | −60 $p > 0.5$ (NS) | −72 $p > 0.1$ (NS) |

NS = not statistically significant at the 5% level.

We claim:

1. A method of treating periodontal disease, which method comprises applying a non-toxic electron acceptor in topically retainable form specifically to the gingival sulcus or crevice or periodontal pocket of the mouth in a therapeutically or prophylactically effective amount sufficient to treat said periodontal disease, said electron acceptor, on said topical application, not supplying molecular oxygen.

2. A method according to claim 1 wherein the electron acceptor is applied in association with a topically retainable carrier therefor.

3. A method according to claim 1 wherein the electron acceptor comprises a non-toxic compound of a multi-valence state metal.

4. A method according to claim 3 wherein the multi-valence state metal comprises iron (III).

5. A method according to claim 1 wherein the electron acceptor has a reduction potential which is positive.

6. A method according to claim 1 wherein the electron acceptor comprises the oxidised form of a redox organic dye.

7. A method according to claim 6 wherein the dye comprises methylene blue or patent blue V.

8. A method according to claim 1 wherein the electron acceptor is insoluble in saliva.

9. A method according to claim 2 wherein the carrier is a gel.

* * * * *